United States Patent [19]

Turnbull et al.

[11] Patent Number: 4,746,677

[45] Date of Patent: May 24, 1988

[54] PYRROLIDINE DERIVATIVES, INSECTICIDAL COMPOSITIONS AND USE

[75] Inventors: Michael D. Turnbull, Reading; Ian T. Kay, Penzance, both of England

[73] Assignee: Imperial Chemical Industries PLC, London, England

[21] Appl. No.: 68,526

[22] Filed: Jul. 1, 1987

Related U.S. Application Data

[62] Division of Ser. No. 941,101, Dec. 12, 1986, Pat. No. 4,696,926.

[30] Foreign Application Priority Data

Dec. 19, 1985 [GB] United Kingdom ................ 8531284
Dec. 19, 1985 [GB] United Kingdom ................ 8531285

[51] Int. Cl.⁴ .................... A01N 43/36; C07D 207/08
[52] U.S. Cl. .................... 514/423; 514/428; 548/539; 548/540; 548/570
[58] Field of Search ............ 548/539, 540, 570; 514/423, 428

[56] References Cited

U.S. PATENT DOCUMENTS 3,459,768 8/1969 Monsimer et al. ................ 548/570

4,353,900 10/1982 Clark ................ 544/71

FOREIGN PATENT DOCUMENTS 0163319 12/1985 European Pat. Off. .

Primary Examiner—Robert W. Ramsuer
Attorney, Agent, or Firm—Cushman, Darby & Cushman

[57] ABSTRACT

A compound of formula (I):

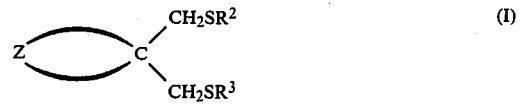

or a salt thereof;

wherein Z represents a heterocyclic ring and $R^2$ and $R^3$ are independently selected from hydrogen, nitrile, $CONH_2$, and $SO_2R^4$ wherein $R^4$ is optionally substituted aryl, optionally substituted alkyl, aralkyl or cycloalkyl or $R^2$ and $R^3$ together form an optionally substituted methylene group or a bond, intermediates, compositions, insecticidal and nematicidal use.

4 Claims, No Drawings

PYRROLIDINE DERIVATIVES, INSECTICIDAL COMPOSITIONS AND USE

This is a division of application Ser. No. 941,101, filed Dec. 12, 1986, now U.S. Pat. No. 4,696,926.

The present invention relates to novel heterocyclic derivatives which have biological activity, in particular insecticidal activity to processes for preparing these derivatives and to compositions containing them.

British Patent Application No. 1264207 describes pesticidal compositions containing a compound of formula A

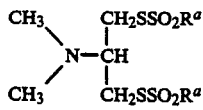

where $R^a$ groups may be the same or different and each represents a $C_{1-4}$ alkyl group, an ethoxyethyl group, a 2-tetrahydrofurylmethyl group or a group

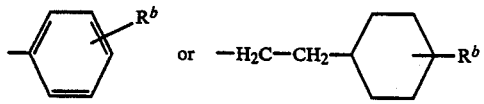

wherein $R^b$ is hydrogen, $C_{1-2}$ alkoxy, $C_{1-2}$ alkylthio or halogen. Further related pesticidal compounds and processes for their preparation are described in EP-A-0104352 and EP-A-102062.

According to the present invention there is provided a compound of formula (I)

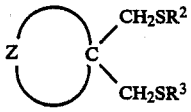

or a salt thereof; wherein

Z represents a heterocyclic ring;

$R^2$ and $R^3$ are independently selected from hydrogen; nitrile; $CONH_2$ and $SO_2R^4$ wherein $R^4$ is optionally substituted aryl, optionally substituted alkyl, aralkyl or cycloalkyl or $R^2$ and $R^3$ together form an optionally substituted methylene group or a bond.

As used herein, the term "aryl" includes phenyl and naphthyl.

Suitably Z is a heterocyclic ring containing 5 or 6-ring atoms up to 3 of which are selected from oxygen, nitrogen and sulphur. Preferably the ring contains a moiety $NR^1$ wherein $R^1$ is alkyl, aralkyl or acyl.

Suitable heterocyclic groups

include morpholino and pyrrolidyl, such as 2,2 or 3,3 disubstituted morpholines and 2,2 disubstituted pyrrolidines.

Suitable groups $R^1$ include $C_{1-6}$ alkyl, benzyl and

wherein $R^5$ is a hydrocarbyl group such as $C_{1-6}$ alkyl or aryl.

Suitably $R^1$ is methyl, ethyl or benzyl, preferably methyl.

Examples of optional substituents for $R^4$ when $R^4$ is aryl include up to three groups selected from $C_{1-4}$ alkyl, halogen such as fluorine, chlorine, bromine or iodine, $C_{1-4}$ alkoxy and $C_{1-4}$ alkylthio.

When $R^4$ is alkyl, it suitably contains from 1 to 4 carbon atoms and may be optionally substituted by straight or branched $C_{1-4}$ alkoxy groups.

Suitable aralkyl groups $R^4$ contain from 7 to 10 carbon atoms such as benzyl, phenethyl or phenylpropyl.

Suitable cycloalkyl groups $R^4$ contain from 4 to 7 carbon atoms.

Preferably $R^2$ and $R^3$ are the same and are both nitrile, $-SO_2(C_6H_5)$ or

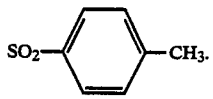

When $R^2$ and $R^3$ together form an optionally substituted methylene group suitable examples include

wherein one or both of $R^6$ or $R^7$ is an electron withdrawing group and where necessary the other is hydrogen, optionally substituted hydrocarbon or optionally substituted heterocyclyl; or $R^6$ and $R^7$ together form a carbocyclic ring provided that at least one of $R^6$ or $R^7$ is a carbonyl group.

Examples of suitable electron withdrawing groups for $R^6$ or $R^7$ include nitrile, nitro, $COOR^8$ where $R^8$ is hydrogen or hydrocarbon such as $C_{1-6}$ alkyl, $SO_2R^4$ where $R^4$ is as hereinbefore defined, $CONR^9R^{10}$ where $R^9$ and $R^{10}$ are the same or different and each is a hydrogen atom, $C_{1-4}$ alkylaminocarbonyl or a hydrocarbon group such as $C_{1-6}$ alkyl which may optionally be substituted.

Preferably both $R^6$ and $R^7$ are electron withdrawing groups, in particular $-COOR^8$ where $R^8$ is a $C_{1-6}$ alkyl such as ethyl.

Examples of suitable optionally substituted hydrocarbon groups for $R^6$ or $R^7$ include optionally substituted alkyl groups of 1 to 15 carbon atoms, cycloalkyl groups of 3 to 6 carbon atoms, alkenyl groups of 2 to 4 carbon atoms, cycloalkenyl groups of 3 to 6 carbon atoms, aryl and aralkyl groups of 7 to 10 carbon atoms, such as benzyl or phenylethyl. Examples of suitable optionally substituted heterocyclic groups include optionally substituted 5- to 6-membered heterocyclic groups containing oxygen, sulfur and/or nitrogen atoms as heteroatoms, such as thienyl, furyl, pyrazolyl, thiazolyl, isothiazolyl, oxazolyl, isooxazolyl, diazolyl, triazolyl, tetrazolyl, pyridyl, pyrimidyl, pyridazinyl, quinolyl, isoquinolyl, indolyl, etc.

Suitable optional substituents for these hydrocarbon and heterocyclic groups are one or more, preferably 1 or 2, groups selected from nitro, amino, hydroxy, cyano, carbamoyl, carboxyl, sulfo, halogen such as fluorine, chlorine, bromine, iodine, trifluoromethyl, methylenedioxy, $C_{1-4}$ alkoxy groups hydroxy-$C_{1-4}$ alkoxy group, phenoxy and benzoyl.

A preferred substituted hydrocarbon group for $R^6$ or $R^7$ is p-chlorophenyl.

A further example of a compound of formula (I) are compounds where $R^2$ and $R^3$ together form a bond.

Suitable salts of the compound of formula (I) are any agriculturally acceptable salts such as acid addition salt with an inorganic acid, for example, hydrochloric acid, hydrobromic acid, sulphuric acid or phosphoric acid, or an organic acid for example benzenesulfonic acid, p-toluene sulphonic acid, oxalic acid, acetic acid or maleic acid.

A preferred sub-group of compounds of formula (I) are compounds of formula (IA)

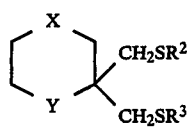
(IA)

wherein $R^2$ and $R^3$ are as hereinbefore defined and one of X or Y is oxygen and the other is $NR^1$ where $R^1$ is as hereinbefore defined.

A further preferred sub-group of compounds of formula (I) are compounds of formula (IB)

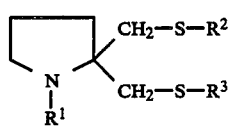
(IB)

wherein $R^1$, $R^2$ and $R^3$ are as hereinbefore defined.

Examples of compounds of the invention are the compounds set out in Tables I, II, III and IV together with salts thereof.

TABLE I

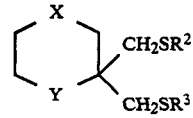

| Compound No. | $R^2$ | $R^3$ | X | Y |
|---|---|---|---|---|
| 1 | $SO_2(C_6H_5)$ | $SO_2(C_6H_5)$ | —O— | \NCH_3/ |
| 2 | CN | CN | —O— | \NCH_3/ |
| 3 | $SO_2$—C_6H_4—CH_3 | $SO_2$—C_6H_4—CH_3 | —O— | \NCH_3/ |

TABLE I-continued

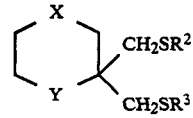

| Compound No. | $R^2$ | $R^3$ | X | Y |
|---|---|---|---|---|
| 4 | CN | CN | —O— | \NCH_3/ |

TABLE II

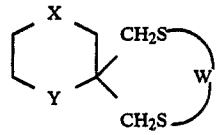

| Compound No. | W | X | Y |
|---|---|---|---|
| 5 | \C(CO_2CH_2CH_3)_2/ | —O— | \NCH_3/ |
| 6 | \C(—C_6H_4—Cl)(CN)/ | —O— | \NCH_3/ |
| 7 | bond | —O— | \NCH_3/ |
| 8 | bond | —O— | \NCH_3/ |

TABLE III

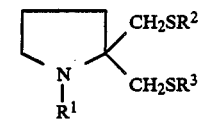

| Compound No. | $R^1$ | $R^2$ | $R^3$ |
|---|---|---|---|
| 9 | $CH_3$ | $SO_2Ph$ | $SO_2Ph$ |
| 10 | $CH_3$ | $SO_2$—C_6H_4—CH_3 | $SO_2$—C_6H_4—CH_3 |
| 11 | $CH_2CH_3$ | $SO_2Ph$ | $SO_2Ph$ |
| 12 | $CH_2CH_3$ | $SO_2$—C_6H_4—CH_3 | $SO_2$—C_6H_4—CH_3 |
| 13 | —$CH_2Ph$ | $SO_2Ph$ | $SO_2Ph$ |
| 14 | —$CH_2Ph$ | $SO_2$—C_6H_4—CH_3 | $SO_2$—C_6H_4—CH_3 |

TABLE IV

| Compound No. | R¹ | Z″ |
|---|---|---|
| 15 | $CH_3$ |  |
| 16 | $CH_3$ | bond |
| 17 | $CH_3$ | 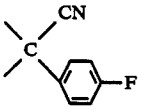 |
| 18 | $CH_3$ | 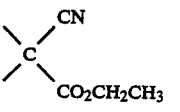 |
| 19 | $CH_2CH_3$ | 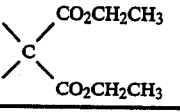 |

Compounds of formula (I) can be prepared by conventional methods for example by reaction of a compound of formula (II)

 (II)

wherein Z' is Z as hereinbefore defined or a group reducible to Z and $R^8$ and $R^9$ are leaving groups with a compound of formula (III)

$$Q(SR^2)_n \quad (III)$$

wherein Q is a cation of valency n and $R^2$ is as hereinbefore defined; and thereafter if desired carrying out one or more of the following steps
(i) reducing Z' to Z; and
(ii) converting one or both groups $R^2$ to other $R^2$ and $R^3$ groups
Examples of group

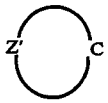

include 2- or 3-morpholino, or 1-methyl-2-pyrrolidinone.

Suitable leaving groups $R^8$ and $R^9$ include halogen such as chlorine or p-toluenesulphonate.

Examples of cations Q include alkali metal ions such as sodium or potassium.

Other preparations can be carried out depending upon the nature of the group Z.

Compounds of formula (IA) wherein $R^2$ and $R^3$ are the same are suitably prepared by reaction of a compound of formula (IV)

 (IV)

wherein X and Y are as defined in relation to formula (IA) and $R^8$ and $R^9$ are leaving groups; with a compound of formula (V):

$$M^{n+}(SR^2)_n \quad (V)$$

wherein $R^2$ is as defined in relation to formula (I) and M is a metal ion of valency n where n is an integer of from 1 to 3. Suitable leaving groups $R^8$ and $R^9$ are halogen such as chlorine. Examples of suitable metal ions M include alkali metals such as sodium or potassium.

The reaction is suitably carried out in an organic solvent such as lower alcohols for example methanol or ethanol. Preferably the reaction is conducted at elevated temperatures of from 40° C. to the boiling point of the solvent, most preferably under reflux conditions.

Particular examples of compounds of formula (III) are sodium benzenethiosulphonate and potassium thiocyanate.

The compounds of formula (I) prepared in this way can be converted to compounds of formula (I) where $R^2$ and/or $R^3$ are different such groups by conventional methods.

For example, compounds of formula (I) with $R^2$ and $R^3$ being $SO_2R^4$ can be obtained by the method described above. These compounds can then be reacted with compounds of formula (VI):

 (VI)

wherein $R^6$ and $R^7$ are as defined above to form compounds of formula (I) wherein $R^2$ and $R^3$ together form an optionally substituted methylene group. The precise reaction conditions will depend upon the nature of compound of formula (VI). Suitably the reaction is carried out in an organic solvent such as chloroform, preferably in the presence of a base such as triethylamine or diazabicycloundecane (DBU). Elevated temperatures of from 50° C. to the boiling point of the solvent are suitably employed.

Alternatively, compounds of formula (IA) wherein $R^2$ and $R^3$ are —CN can be converted to compounds of formula (IA) wherein $R^2$ and $R^3$ form a bond by reaction with a strong base such as potassium hydroxide. The reaction is suitably carried out in an organic solvent such as ethanol or methanol.

Compounds of formula (IV) can be prepared by reaction of a compound of formula (VII):

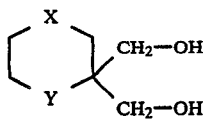

wherein X and Y are as hereinbefore defined with an appropriate derivitising reagent. Examples of suitable derivitising reagents include halogenating agents such as thionyl chloride, or phosphorus tribromide; or an agent which will introduce a leaving group such as para-toluene sulphonyl chloride or methane sulphonyl chloride.

The reaction is suitably carried out in an inert organic solvent such as chloroform at an elevated temperature of for example from 40° C. to the boiling point of the solvent.

Compounds of formula (VII) can be prepared by acid hydrolysis of compound of formula (VIII):

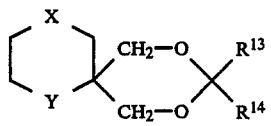

wherein X and Y are as defined in relation to formula (IA) and $R^{13}$ and $R^{14}$ are $C_{1-6}$ alkyl groups such as methyl. Suitable acids for use in the hydrolysis include inorganic acids such as hydrochloric acid.

Compounds of formula (VIII) can be prepared by reduction of a compound of formula (IX):

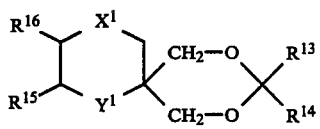

wherein $X^1$ and $Y^1$ are X and Y as defined in relation to formula (IA) or one of $X^1$ or $Y^1$ is oxygen and the other is $NR^1$ or —NH—; $R^{13}$ and $R^{14}$ are as defined in relation to formula (VIII) and one of $R^{15}$ or $R^{16}$ is oxo and the other is hydrogen provided that the said oxo group is adjacent to the —NH— or $NR^1$ group. Reduction is suitably carried out by conventional methods for example by using a reducing agent such as lithium aluminium hydride, in an inert organic solvent such as tetrahydrofuran.

Compounds of formula (IX) can be prepared by cyclisation of a compound of formula (X):

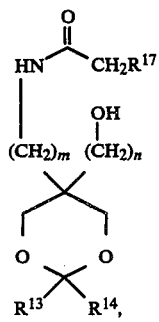

wherein $R^{13}$ and $R^{14}$ are as defined in relation to formula (IX); one of m or n is 1 and the other is zero; and $R^{17}$ is halogen such as chlorine.

Cyclisation can be effected using a base such as potassium tert-butoxide. The reaction is suitably carried out in an inert organic solvent such as tertiary butanol at moderate temperatures of from 10° C. to 60° C., conveniently at ambient temperature.

Compounds of formula (X) can be prepared by reaction of compounds of formula (XI):

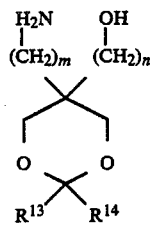

wherein $R^{13}$ and $R^{14}$ are as defined in relation to formula (VIII) and m and n are as defined in relation to formula (X); with a compound of formula (XII):

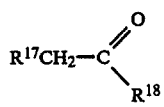

wherein $R^{17}$ is as defined in relation to formula (XI) and $R^{18}$ is halogen such as chlorine.

The reaction is suitably carried out in an inert organic solvent such as methylene chloride at depressed temperatures of from −40° C. to 10° C.

Compounds of formula (XI) are either known compounds (see J C S Perkin II 1974 p. 402) or can be prepared from known compounds by known methods.

Compounds of formulae (IV), (VII), (VIII), and (X) are novel and as such form part of the invention.

The compounds of formula (IB) or salts thereof can be prepared by reacting a compound of formula (XIII)

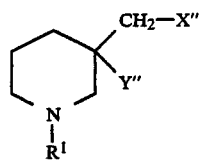

wherein
$R^1$ is as defined in relation to formula (IB);
X" and Y" are the same or different and are both leaving groups;
with a compound of formula (XIV)

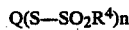

$$Q(S—SO_2R^4)_n \qquad (XIV)$$

wherein $R^4$ is as hereinbefore defined and Q is an cation of valency n, where n is 1, 2 or 3, to form a compound of formula (I) wherein $R^2$ and $R^3$ are $SO_2R^4$ and thereafter if desired converting the groups $R^2$ and/or $R^3$ to different such groups.

Examples of suitable leaving groups for X" and Y" include halo such as chloro or bromo, tosylate or mesylate.

Examples of suitable cations Q include alkali metal ions such as sodium.

The reaction is suitably carried out in an organic solvent such as ethanol or acetonitrile at elevated temperatures for example of from 50° C. to the boiling point of the solvent.

Conversion of the groups $R^2$ and $R^3$ to different such groups can be carried out by conventional methods, for example, compounds where $R^2$ and $R^3$ form a methylene group substituted with two carboxylic ester groups can be prepared by reacting the compound of formula (IB) wherein $R^2$ and $R^3$ are $SO_2R^4$ with the appropriate malonate ester, preferably in the presence of a base such as triethylamine. This reaction is suitably carried out in an organic solvent such as chloroform, or toluene. Again, it is preferable to use elevated temperatures for example of from 50° C. to the boiling point of the solvent.

Alternatively, the compound of formula (IB) wherein $R^2$ and $R^3$ are $SO_2R^4$ can be reacted with a compound of formula $H_2CR^2R^3$ wherein $R^2$ and $R^3$ are as hereinbefore defined. For example reaction with parachlorobenzylcyanide in the presence of a base such as diazobicycloundecene (DBU), will produce a compound of formula (IB) wherein $R^2$ is nitrile and $R^3$ is p-chlorophenyl. The reaction is suitably carried out in an organic solvent such as chloroform at an elevated temperature of from 50° C. to the boiling point of the solvent.

Compounds of formula (IB) wherein $R^2$ and $R^3$ together form a bond can be prepared by cyclisation of a compound of formula (IB) wherein $R^2$ and $R^3$ are removable groups. For example when $R^2$ and $R^3$ are both nitrile, reduction using a reducing agent such as lithium aluminium hydride followed by aerial oxidation of the thiol intermediate will yield the desired cyclic product.

Compounds of formula (XIII) can be prepared by reaction of a compound of formula (XVI)

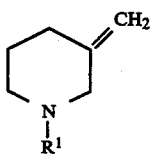 (IV)

wherein $R^1$ is as hereinbefore defined in relation to formula (IB) with a compound of formula (XVI)

X''—Y''0 (XVI)

where X'' and Y'' are as defined in relation to formula (XIII). Preferably X''—Y'' is a halogen such as chlorine.

Compounds of formula (XV) are known compounds or can be prepared from known compounds such as the equivalent piperidones, by conventional methods.

Alternatively the compounds of formula (XVIII) can be prepared by reacting a compound of formula (XVII)

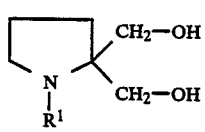 (XVII)

wherein $R^1$ is as defined in relation to formula (I) with a compound of formula (XVI) as hereinbefore defined.

A preferred compound of formula (XVI) in this instance is p-toluene sulphonyl chloride. The reaction is suitably carried out in an organic solvent such as dichloromethane in the presence of a base such as triethylamine. Moderate temperatures of from 0° C.-30° C., conveniently ambient temperature, are employed.

Compounds of formula (XVIII) can be prepared by acid hydrolysis of a compound of formula (XIX):

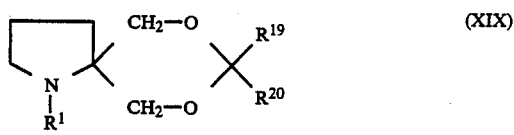 (XIX)

wherein $R^1$ is as defined in relation to formula (I) and $R^{19}$ and $R^{20}$ are $C_{1-6}$ alkyl groups such as methyl. The reaction is suitably effected having an aqueous inorganic acid such as hydrochloric acid.

Compounds of formula (XIX) can be prepared by reduction of a compound of formula (XX):

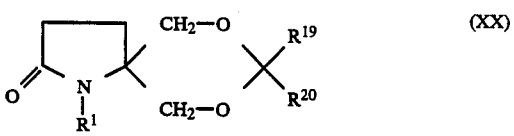 (XX)

wherein $R^1$ is as defined in relation to formula (I) and $R^{19}$ and $R^{20}$ are as defined in relation to formula (XIX).

The reduction is suitably carried out using a reducing agent such as lithium aluminium hydride in an inert organic solvent such as tetrahydrofuran.

Compounds of formula (XX) can be prepared by reaction of a compound of formula (XXI):

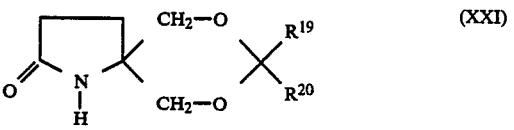 (XXI)

wherein $R^{19}$ and $R^{20}$ are as defined in relation to formula (XIX), with a compound of formula (XXII):

$R^1$—$R^{21}$ (XXII)

wherein $R^1$ is as defined in relation to formula (IB) and $R^{21}$ is halogen such as iodine, in the presence of a base such as sodium hydride. The reaction is suitably carried out in an inert organic solvent such as tetrahydrofuran, and under an inert atmosphere of for example nitrogen.

Compounds of formula (XXI) can be prepared by reductive cyclisation of a compound of formula (XXIII):

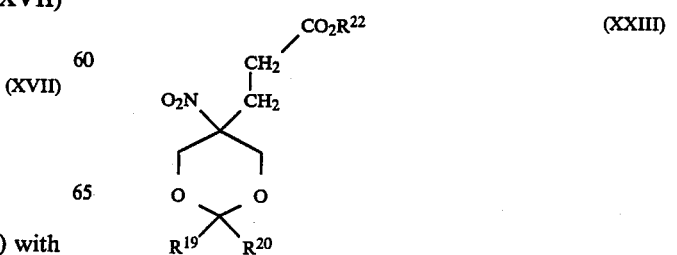 (XXIII)

wherein $R^{19}$ and $R^{20}$ are as defined in relation to formula (XIX) and $R^{22}$ is $C_{1-6}$ alkyl such as methyl.

The reaction can be carried out by reaction with a metal such as zinc in the presence of an acid such as acetic acid. Preferably an inert organic solvent such as tetrahydrofuran, is employed and the reaction is effected under an inert atmosphere of for example nitrogen.

Compounds of formula (XXIII) can be prepared by reacting a compound of formula (XXIV):

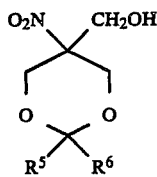

(XXIV)

wherein $R^5$ and $R^6$ are as defined in relation to formula (XIX); with a compound formula (XXV):

(XXV)

wherein $R^{22}$ is as defined in relation to formula (XXIII) in the presence of a base such as sodium methoxide.

The reaction is suitably carried out in an organic solvent such as methanol and at moderate temperatures, conveniently at ambient temperature.

Compounds of formula (XXIV) or (XXV) are known compounds or can be produced from known compounds by conventional methods.

Compounds of formula (IB) may also be prepared by reduction of a compound of formula (XXVI):

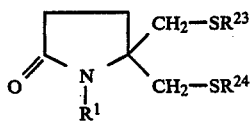

(XXVI)

wherein $R^1$ is as defined in relation to formula (I) and $R^{23}$ and $R^{24}$ are the same and are equivalent to $R^2$ and $R^3$ or are groups reducible to $R^2$ and $R^3$. The reduction is carried out using a reducing agent, selected such that it reduces the carbonyl group on the pyrrolidine ring and optionally also the groups $R^{23}$ and $R^{24}$. The reaction conditions are suitably those conventional for the particular reducing agent employed.

For example when $R^{22}$ and $R^{24}$ are both nitrile, reduction using lithium aluminium hydride will produce a compound of formula (I) wherein $R^2$ and $R^3$ form a bond.

Compounds of formula (XXVI) are suitably prepared by reacting a compound of formula (XXVII):

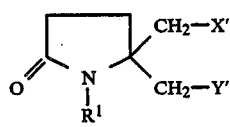

(XXVII)

wherein $R^1$ is as defined in relation to formula (I) and $X'$ and $Y'$ are leaving groups with a compound of formula (XXVIII):

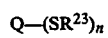

(XXVIII)

where $R^{23}$ is as defined in relation to formula (XXVI) and Q and n are as hereinbefore defined in relation to formula (XIV).

Preferred examples of $X'$ and $Y'$ are p-toluenesulphonate.

Preferably Q is an alkali metal ion such as potassium.

The reaction is suitably carried out in an inert organic solvent such as dimethylformamide at an elevated temperature of from 100° C. to the boiling point of the solvent.

Compounds of formula (XXVII) can be prepared by reacting a compound of formula (XXIX):

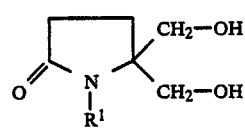

(XXIX)

wherein $R^1$ is as defined in relation to formula (IB), with an appropriate derivitising reagent, such as p-toluene sulphonyl chloride.

The reaction is suitably effected in an organic solvent such as pyridine.

Compounds of formula (XXIX) can be prepared by hydrolysis of a compound of formula (XX) as hereinbefore defined in the presence of a strong acid such as trifluoroacetic acid or hydrochloric acid.

The compounds of formula (I) have insecticidal-/acaricidal activity. They are particularly useful as nematocides. They can be applied in any of the forms conveniently employed in agriculture. Thus in a further aspect, the invention provides a method of killing or controlling insect or nematode pests which method comprises administering to the insect or to the locus thereof, an effective amount of a compound of formula (I).

The compounds are suitably applied in the form of a composition. Therefore a further aspect of the invention comprises an insecticidal or nematocidal composition comprising a compound of formula (I) as hereinbefore defined on a salt thereof in combination with an agriculturally acceptable carrier.

Thus depending on the intended use, one or more compounds of formula (I) are either dissolved or dispersed in a suitable liquid vehicle or admixed with or adsorbed on a suitable solid vehicle and the resulting composition is made available in any of such forms as emulsifiable concentrate, oil, wettable powder, dusts, granules, tablets, aerosol mist, ointment, etc. There may also be added to these preparations such additives as emulsifiers, suspending agents, extenders, penetrants, wetting agents, thickners or stabilizers, as necessary. These preparations can be produced by the known methods.

The proportion of the compound of formula (I) in such an insecticidal/acaricidal/nematocidal preparation depends on the intended use and application. In the case of an emulsifiable concentrate or wettable powder, the range of about 10 to 90 weight percent is desirable, while the range of about 0.1 to 10 weight % is suitable for an oil or dust. Granules may preferably contain about 1 to 20 weight % of the compound of formula (I). In using the emulsifiable concentrate or wettable powder, it is preferable to dilute the concentrate or powder to a suitable concentration (e.g. 100- to 100000-fold), for example with water.

The rate at which the compounds as applied will depend upon a number of factors, such as degree of infestation etc. However, in general, a rate of from 0.5 kg/ha to 40 kg/ha of active ingredient will be suitable.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Insecticides in the active soil will be particularly useful in these cases. Examples of suitable insecticides include the following:

(a) Pyrethroids such as permethrin, esfenvalerate, deltamethrin, cyhalothrin in particular, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphosmethyl, fenitrothion or diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl.

Examples of suitable insecticide synergists for use in the compositions include piperonyl butoxide, sesamax, and dodecyl imidazole.

Suitable herbicides, fungicides and plant growth regulators for inclusion in the compositions will depend upon the intended target and the effect required.

The ratio of the compound of the invention to the other active ingredient in the composition will depend upon a number of factors including type of target, effect required from the mixtures etc.

However in general, the additional active ingredient of the composition will be applied at about the rate as it is usually employed, or at a slightly lower rate if synergism occurs.

The following Examples illustrate the invention.

EXAMPLE 1

This Example illustrates the preparation of Compound No. 1 in Table I.

Example 1a

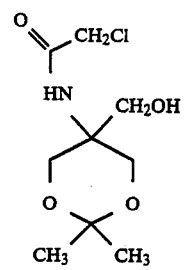
(i)

1.9 g chloroacetyl chloride in 10 ml methylene chloride was added dropwise, at 0° to −5°, to a solution of 5-amino-5-hydroxymethyl-2,2-dimethyl-1,3-dioxan, (prepared as described in J C S Perkin II 1974, 402) (2.5 g) and triethylamine (1.7 g) in 40 ml methylene chloride. The reaction was stirred at 0° to −5° for 30 minutes and then allowed to warm to room temperature before evaporating in vacuo. The residue was treated with approximately 30 ml ethyl acetate and filtered (from triethylamine hydrochloride). The ethyl acetate was evaporated in vacuo to give a sticky, off-white solid which was chromatographed on silica, using ethyl acetate eluant, to give compound (i) above as a light yellow crystalline solid. This was recrystallised from 60–80 petrol-Ethyl acetate. Yield 2.0 g mp. 92°–4°.

NMR (1.4, s, 6H; 3.7, d, 2H; 3.8, q, 4H; 4.0, s, 2H; 4.3, t, 1H; 7.2, s, 1H)

Example 1b

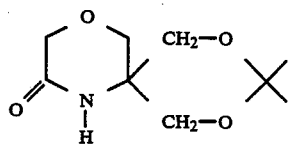
(ii)

Compound (i) (5.8 g), prepared as described in Example 1a, in 50 ml tert-butanol was added dropwise at room temperature, over a period of 2½ hours to a solution of potassium tert-butoxide (5.4 g) in 70 ml tert-butanol. The reaction was stirred at room temperature for a further 2 hours and then left to stand overnight. The tert-butanol was evaporated in vacuo and the residue dissolved in approximately 30 ml water and neutralised to pH 7 with 2N hydrochloric acid. The resulting solution was extracted (4X) with CH$_2$Cl$_2$, the combined extracts dried (MgSO$_4$) and evaporated in vacuo to give compound (ii) above as a colourless solid which was recrystallised from 60–80 petrol and ethyl acetate. Yield 3.5 g mp. 164°–6°.

NMR (1.4, 2s, 6H; 3.7, s, 4H; 4.0, s, 2H; 7.7, s, 1H)

Example 1c

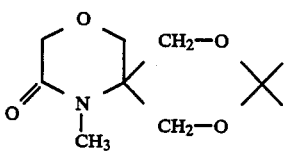
(iii)

Sodium hydride (4.5 g of a 50% dispersion in oil) was washed free of oil with 40–60 petrol and suspended in tetrahydrofuran (THF) (40 ml). Compound (ii) (18.0 g), prepared as described in Example 1b, in 160 ml THF was then added dropwise, under an atmosphere of N₂, at room temperature and the resulting brown solution stirred for an additional 1½ hours. Methyl iodide (15 g) was then added and the reaction stirred for 2 hours and left overnight. The THF was evaporated in vacuo and the resulting brown oil dissolved in a small volume of water and extracted with CH₂Cl₂ (3x). The combined extracts were dried over MgSO₄ and evaporated in vacuo to give an orange oil (17.6 g) which crystallised on standing. A small sample was distilled (in Kugelrohr oven) to give compound (iii) above as a colourless oil which again crystallised on standing. bp. (oven temp) 105°-110°/0.03 mbar NMR 1,3, s, 3H; 1.4, s, 3H; 3.1, s, 3H; 3.7, q, 4H; 3.7, s, 2H; 4.1, s, 2H)

Example 1d

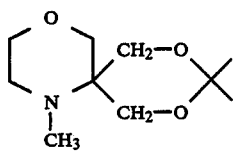

(iv)

Compound (iii) (5.0 g) from Example 1c was dissolved in dry THF (50 ml) and added dropwise, under an atmosphere of N₂ at room temperature, to a stirred suspension of LiAlH₄ (0.9 g) in dry THF (10 ml) giving a slightly exothermic reaction. The reaction was then heated under reflux for 2 hours before cooling to 5° and carefully adding a saturated solution of sodium potassium tartrate. The mixture was stirred vigorously for approximately 20 minutes and then the organic layer separated. The aqueous solution was extracted (1x) with ethyl acetate. The organic solutions were combined, washed with a small volume of saturated brine, dried (MgSO₄) and evaporated in vacuo to give crude compound (iv) above as a colourless oil. Distillation under high vacuum in kugelrohr oven gave pure product, 3.9 g bp. (oven temp) 80°-90°/0.03 mbar.

NMR 1.3, s, 3H; 1.4, s, 3H; 2.5, s, 3H; 2.5, m, 2H; 3.5, s, 2H; 3.55, d, 2H; 3.6, m, 2H; 3.85, d, 2H

Example 1e

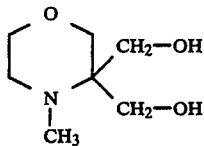

(v)

The product from Example 1d (3.9 g) in 2N hydrochloric acid (25 ml) was stirred at room temperature for 3 hours and then neutralised with approximately 10N sodium hydroxide solution. The resulting solution was extracted with CHCl₃ (in continuous extraction apparatus) for 14 hours and then the CHCl₃ dried (MgSO₄) and evaporated in vacuo to give crude compound (v) above as an orange, highly viscous oil (2.2 g).

NMR 2.4, s, 3H; 2.7, m, 2H; 3.3, s, 2H; 3.5, d, 2H; 3.7, m, 6H

Example 1f

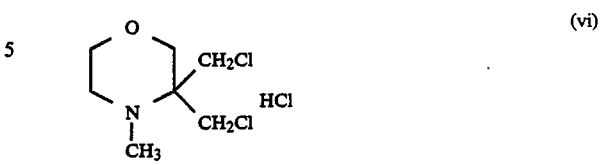

(vi)

Compound (v) (2.1 g) from Example 1e was dissolved in 3 ml chloroform and added dropwise, at 5°, to thionyl chloride (6 ml). The resulting solution was heated under reflux for 3 hours (solution turns red). Mixture was then evaporated in vacuo to give a sticky red solid which gave a yellow crystalline solid on trituration with acetone. The solid was filtered, dried and recrystallised from acetone-ethanol to give compound (vi) above as light-yellow prisms, (1.1 g). mp. 172°-6° (dec).

NMR 3.0, s, 3H; 3.5, t, 2H; 4.0, t, 2H; 4.1, d and s, 4H; 4.3, d, 2H

Example 1g

Compound (vi) (4g), prepared as described in Example 1f was dissolved in water and neutralized by the addition of 8.3 ml 2N sodium hydroxide solution. The solution was extracted with dichlormethane (3x), the combined extracts dried (MgSO₄) and evaporated in vacuo at 25° to give the free base as a colourless oil (3.4 g). This was dissolved in ethanol (70 ml), sodium benzenethiosulphonate (6.6 g) added and the solution heated under reflux for 2 hours. The mixture was then filtered hot and the filtrate cooled to room temperature to give a crude product as pale yellow crystals (5.9 g) mp. 115°-6° Recrystallisation from methanol gave pure compound 1 in Table I as colourless prisms. mp. 117°-118°.

NMR 2.2, s, 3H; 2.5, m, 2H; 3.0, d, 2H; 3.4, s, 2H; 3.45, d, 2H; 3.6, m, 2H: 7.6, m, 6H; 7.9, m, 4H

EXAMPLE 2

This Example illustrates the preparation of Compound No. 2 in Table I.

Compound (vi) (2.47 g) prepared as described in Example 1f, was dissolved in water and neturalised by the addition of 2N sodium hydroxide solution. The solution was extracted with CH₂Cl₂ (3x) and the combined extracts dried (MgSO₄) and evaporated in vacuo to yield the free base as a colourless oil. This was dissolved in methanol (60 ml), 2.05 g potassium thiocyanate added and the reaction heated under reflux for 3½ hours. The mixture was filtered hot and the filtrate cooled to room temperature to give compound No. 2 in Table I as colourless crystals (1.5 g). mp. 120°-4°.

EXAMPLE 3

This Example illustrates the preparation of Compound No. 3 in Table I.

This compound was prepared from compound (vi) by method analogous to that described in Example 1(g) above except that the final crystallisation step was carried out using iso-propanol to yield the desired compound (mp. 93°-4° C.).

NMR: 2,2, 3H; 2.5, s, 6H; 2.55, t, 2H; 3.0, d, 2H; 3.4, s, 2H; 3.45, d, 2H; 3.6, t, 2H; 7.45, d, 4H; 7.8, d, 4H

EXAMPLE 4

This Example illustrates the preparation of the oxalate salt of compound No. 4 in Table I.

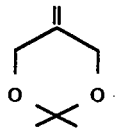
(vii)

EXAMPLE 4a

3-Hydroxy-2-hydroxymethyl-1-propene, (prepared from 3-chloro-2-(chloro methyl)-1-propene as described in De. O.S, 2,247,030) (43,0 g), acetone (400 ml), 2,2-dimethoxypropane (100 ml) and p-toluenesulphonic acid (100 mg) were stirred together at room temperature for 3 hours. The solvents were then distilled at atmospheric pressure and the residual crude product distilled under partially reduced pressure to give compound (vii) as a colourless mobile oil.

bp. 58°-60°/34 mm Hg
Yield 45.0 g (72%)
NMR: 1.5, s, 6H; 4.4, m, 4H; 4.9, m, 2H

EXAMPLE 4b

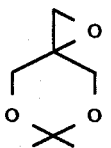
(viii)

m-Chloroperbenzoic acid (76.0 g) was added portionwise to a stirred solution of compound (vii) in dichloromethane (500 ml), at room temperature giving a clear colourless solution. After a few minutes a slightly exothermic reaction began and a white solid was precipitated. The reaction was stirred at room temperature for 6 hours and then left overnight. The mixture was filtered and the precipitate washed with a small amount of dichloromethane. The combined filtrate and washings were washed with a 10% aqueous solution of sodium sulphite followed by saturated aqueous sodium bicarbonate, dried (MgSO4) and evaporated under reduced pressure. The resulting crude product was distilled under water-pump pressure to give compound (viii) as a colourless mobile oil.

bp. 72°-75°/12 mmHg
yield 33.2 g (66%)
NMR: 1.5, s, 6H; 2.8, s, 2H; 3.7, d, 2H; 4.1, d, 2H.

EXAMPLE 4c

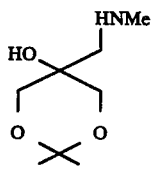
(ix)

Compound (viii) (33.2 g) in ethanol (40 ml) was added dropwise over a period of ca. 30 minutes to a 33% solution of methylamine in ethanol (160 ml) and cooled in ice/water to maintain reaction temperature to from 10°-20° C. The ethanol was then evaporated under reduced pressure to give crude compound (ix) as a colourless oil which crystallised on standing.

yield 38.7 g (96%)
NMR 1.4, 2s, 6H; 2.4, s, 3H; 2.6, s, 2H; 3.7, q, 4H.

EXAMPLE 4d

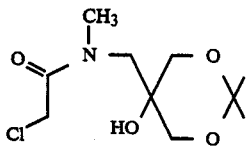
(x)

Chloroacetyl chloride (12.9 g) in dichloromethane (100 ml) was added dropwise, at 0°-5° C., to a solution of compound (ix) (20 g) triethylamine (12.9 g) in dichloromethane (150 ml). The reaction was then allowed to warm to room temperature and stirred for a further 2 hours. The solvent was evaporated under reduced pressure, the residue taken up in ethyl acetate, filtered and the filtrate concentrated under reduced pressure. The concentrated solution was eluted through a short column of silica, using ethyl acetate as eluent, to give compound (x) as a highly viscous yellow oil which crystallised on standing.

Yield 27.4 g (95%)

EXAMPLE 4e

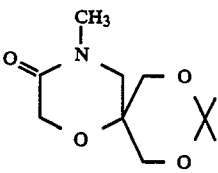
(xi)

Compound (x) 27.4 g) in tert-butanol (300 ml) was added dropwise over a period of 2 hours at room temperature, to a stirred solution of potassium tert-butoxide (12.2 g) in tert-butanol (200 ml). The reaction was stirred for a further 2 hours and then left to stand overnight. After this time the solvent was evaporated under reduced pressure, the residue taken up in water (150 ml) and extracted with dichloromethane (4x). The combined extracts were dried (MgSO4) and evaporated under reduced pressure to give crude compound (xi) as a white solid.

Yield 22.0 g (94%)
NMR: 1.4, 2s, 6H; 3.0, s, 3H; 3.5, s, 2H; 3.8, s, 4H; 4.2, s, 2H.

EXAMPLE 4f

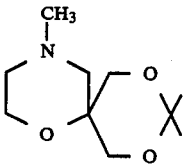
(xii)

Lithium aluminium hydride (0.88 g) was suspended in dry THF (156 ml) and heated to 60°-65° C. under reflux, under an atmosphere of nitrogen. Compound (xi) (5 g) in dry THF (60 ml) was then added dropwise, at 60°-65° C. Reaction was continued for 1 hour after completing the addition and then the mixture was cooled in an ice/water bath and quenched with a saturated aqueous solution of potassium sodium tartrate (50 ml). The resulting mixture was stirred for ½ hour and then the organic layer separated. The aqueous portion was extracted with ethyl acetate (2X) and the extracts combined with the previously separated organic solution. The resulting solution was washed with a small volume of saturated brine, dried (MgSO₄) and evaporated under reduced pressure to give crude compound (xii) as a colourless oil which was distilled under reduced pressure in Kugelrohr apparatus.

bp. (oven temp) 70°–75° C. (0.06 mbar)
Yield 2.9 g (62%)
NMR: 1.4, s, 3H; 1.5, s, 3H; 2.3, s, 3H; 2.35, m, 2H; 2.4, s, 2H; 3.75, m, 2H; 3.8, q, 4H

EXAMPLE 4g

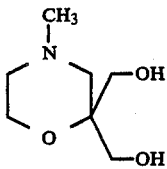
(xiii)

Compound (xii) (2.5 g) were dissolved in methanol (25 ml) and a 2M solution of hydrogen chloride in methanol (25 ml) added in one go, giving a slightly exothermic reaction. The resulting solution was allowed to stand at room temperature for 1 hour and then evaporated under reduced pressure. The residue was dissolved in water (10 ml) and basified with sodium hydroxide pellets. The solution was then extracted with dichloromethane for 14 hours in a continuous extraction apparatus. The dichloromethane was then evaporated under reduced pressure to give compound (xiii) as a colourless viscous oil which crystallised to a "waxy" solid on standing.

Yield 1.86 g (93%)
NMR: 2.3, s, 3H; 2.4, m, 2H; 2.45, s, 2H; 3.7, q, 4H; 3.9, m, 4H

EXAMPLE 4h

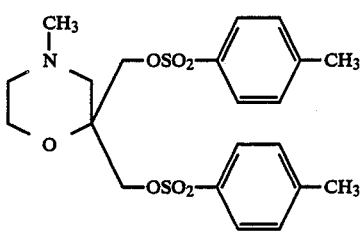
(xiv)

p-Toluenesulphonyl chloride (1.18 g) was added to a solution of compound (xiii) (0.5 g) and 0.63 g triethylamine (6.3 g) in dichloromethane (10 ml) at room temperature. The mixture was stirred at room temperature for 7 hours and then left to stand over the weekend. The mixture was then evaporated under reduced pressure and the residue purified by column chromatography on silica, using ethyl acetate eluent, to give compound (xiv) as a colourless crystalline solid.

Yield 0.60 g (41%)
NMR: 2.15, s, 3H; 2.25, m, 2H; 2,5, s, 6H; 3.6, m, 2H; 3.9, d, 2H; 4.25, d, 2H; 7.35, d, 4H; 7.8, d, 4H.

EXAMPLE 4i

Compound (xiv) (4.0 g) and potassium thiocyanate (8.0 g) in DMF (10 ml) were heated under reflux at 110°–120° for 15 hours. The solution was then cooled to room temperature, water (80 ml) added and extracted with dichloromethane (3x). The combined extracts were dried (MgSO₄) and evaporated under reduced pressure (initially water-pump pressure to remove dichloromethane and then at 50° under high vacuum to remove DMF) to give crude product as a yellow oil. This was dissolved in ether (50 ml) and an excess of a saturated solution of oxalic acid in ether added to give an off-white precipitate of crude product. This was filtered, washed with Et₂O and recrystallised from methanol to give the oxalate salt of compound 4 as off-white prisms.

Yield 0.92 g (32%)
mp. 158°–9° (dec)
NMR (¹³C ppm values): 166.4; 114.8; 74.7; 59.8; 56.0; 52.8; 45.2; 37.9.

| Analysis: | C | H | N |
|---|---|---|---|
| % Expected | 39.63 | 4.53 | 12.60 |
| % Found | 39.55 | 4.51 | 12.66 |

NMR: 2.3, s, 3H; 2.6, t, 2H; 3.1, d, 2H; 3.6, d, 2H; 3.6, t, 2H; 3.7, s, 2H.
IR shows —SCN stretching at 2150 cm⁻¹ (strong)

EXAMPLE 5

This Example illustrates the preparation of Compound No. 5 in Table II.

Compound No. 1 (2.5 g) prepared as described in Example 1g, diethyl malonate (0.85 g) and triethylamine (1.06 g) were dissolved in chloroform (12 ml) and heated under reflux for 48 hours. After this time the mixture was cooled to room temperature, diluted with more chloroform and washed with water (3x). The organic layer was dried (MgSO₄) and evaporated in vacuo to give crude compound 5 as an orange viscous oil. Purification by column chromatography on silica using ethyl acetate eluent gave pure Compound 5 as a light yellow viscous oil (0.54 g).

NMR 1.3, t, 6H; 2.4, s, 3H; 2.6, t, 2H; 2.7, d, 2H; 3.4, d, 2H; 3.7, t, 2H; 3.9, s, 2H; 4.3, q, 4H

EXAMPLE 6

This Example illustrates the preparation of Compound No. 6 in Table II.

Compound No. 1 (2.5 g) prepared as described in Example 1 g, parachlorobenzylcyanide (0.8 g) and DBU (1.6 g) in chloroform (12 ml) were heated under reflux for 10 hours. After this time the mixture was cooled to room temperature, diluted with more CHCl₃ and washed with water (3x). The organic layer was dried (MgSO₄) and evaporated in vacuo to give a yellow oil. Purification by column chromatography on silica, using diethyl ether eluent, gave pure Compound 6 as a white solid which was recrystallised from ethanol to give colourless platelets (0.5 g). mp. 146°–7°.

EXAMPLE 7

NMR 2.5, s, 3H; 2.7, t, 2H; 2.9, d, 2H; 3.7, d, 2H; 3.8, t, 2H; 4.1, s, 2H; 7.4, d, 2H: 7.8, d, 2H

This Example illustrates the preparation of the oxalate salt of Compound No. 7 in Table II.

A solution of potassium hydroxide (0.6 g) in methanol (5 ml) was added dropwise, at 0°, to Compound No. 2 (1.2 g) prepared as described in Example 2 in 25 ml methanol giving a slightly exothermic reaction. The resulting clear solution was placed in a fridge overnight and then poured into water and extracted with chloroform. The chloroform solution was separated and extracted with 2N hydrochloric acid. The hydrochloric acid solution was made alkaline with approximately 10N NaOH solution and extracted with Et₂O (2x). The combined extracts were dried over MgSO₄ and then treated with a 10% solution of oxalic acid in Et₂O to give a yellow 'gum' which crystallised overnight. The solid was filtered and recrystallised from ethanol to give pure Compound 7 as yellow crystals (0.5 g). mp. 124°-5°.

NMR ($^{13}$C): 39.9; 45 (approx-v broad); 54.7; 66.5; 72.8; 78.3; 168.1

EXAMPLE 8

This Example illustrates the preparation of the oxalate salt of compound 8 of Table II.

Compound 4 (1.2 g) from Example 4 was dissolved in methanol (15 ml), cooled in an ice/water bath and treated dropwise with a solution of potassium hydroxide (0.81 g) in methanol (6 ml). After standing overnight in a fridge the mixture was poured into water and extracted with chloroform (2x). The combined extracts were then re-extracted with 2N aqueous hydrochloric acid (2x). The combined HCl extracts were made alkaline with a concentrated aqueous solution of NaOH and extracted with Et₂O (2x). The combined Et₂O extracts were dried (MgSO₄) and treated with an excess of a saturated ether solution of oxalic acid, giving crude product as a pale yellow solid. This was filtered, washed with Et₂O and recrystallised from iso-propanol to give pure product as yellow prisms.

Yield 0.45 g (44%)
mp. 140°-147° C. (dec)
NMR ($^{13}$C, ppm values): 166.4; 86.6; 60.1. 57.6; 53.1; 49.9; 44.9; 43.6

| Analysis: | C | H | N |
|---|---|---|---|
| % Expected | 38.42 | 5.37 | 4.98 |
| % Found | 38.53 | 5.59 | 5.07 |

EXAMPLE 9

This Example illustrates the preparation of Compound No. 9 in Table III in the form of the hydrochloride salt.

EXAMPLE 9a

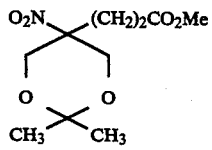 (xv)

Sodium (10 g) was dissolved in 2.8 liters methanol and methyl acrylate (373 g) then dissolved in the resulting solution of sodium methoxide. 5-nitro-5-hydroxymethyl-2,2-dimethyl-1,3-dioxan* (744 g) was then added portionwise (slightly exothermic) and the reaction stirred at room temperature fo 24 hours. (A white solid began to precipitate from the reaction after approximately 1½ hours). After this time the mixture was filtered and compound (xv) obtained as a solid which was washed with a little methanol and dried.

Yield (445 g)
m.p. 95°-8° C.

| Analysis: | C | H | N |
|---|---|---|---|
| % Expected | 48.58 | 6.93 | 5.67 |
| % Found | 47.94 | 6.65 | 5.61 |

5-nitro-5-hydroxymethyl-2,2-dimethyl-1,3-dioxan was prepared as described in J.O.C. *21* 1175-6 (1956).

EXAMPLE 9b

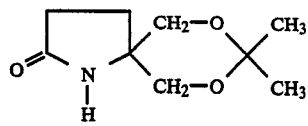 (xvi)

Compound (xv) (27 g) from Example 9a in warm tetrahydrofuran (THF) (30 ml) was added dropwise, under an atmosphere of nitrogen, to a stirred suspension of zinc powder (60 g) in THF (70 ml) and glacial acetic acid (250 ml), heated to 50°-55° (exothermic reaction to 90° C.). After completing the addition the reaction was stirred at 50°-55° for 3¼ hours and then cooled to room temperature. The reaction solution was decanted from unreacted zinc and the zinc washed with acetic acid (2x) and then acetone (2x). The washings were combined with the reaction solution and evaporated "in vacuo" (traces of water or acetic acid being removed by azeotropic evaporation with toluene) to give a pink solid (30 g). This was slurried in dichloromethane (200 ml) and washed with 2M NaOH (aq) (50 ml). The aqueous layer was decanted and extracted with more dichloromethane (4×100 ml). The combined extracts were dried over MgSO₄ and evaporated "in vacuo" to give compound (xvi) (10 g) as a pink solid. This was recrystallised from ethyl acetate to give colourless "plates" (7 g). mp. 170°-173°.

EXAMPLE 9c

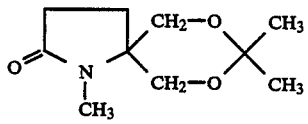 (xvii)

Sodium hydride (3.8 g of a 50% dispersion in oil) was washed free of oil with 40-60 petrol and then suspended in THF (20 ml). Compound (ii) (14.0 g) produced as described in Example 1b, was dissolved in THF (100 ml) and added dropwise under an atmosphere of N₂, at room temperature to the sodium hydride suspension and the resulting solution stirred at room temperature for 1 hour. Methyl iodide (14.0 g) was then added dropwise (slight exotherm) and the reaction stirred at room temperature for a further 3 hours. The THF was then evaporated "in vacuo" and the resulting solid was added to a small amount of water and extracted with CH₂Cl₂ (4x). The combined extracts were dried over MgSO₄ and evaporated "in vacuo" to give crude compound (iii) (13.1 g) as a colourless solid mp. 100°-3°. Recrystallisation from cyclohexane yielded the desired product mp. 105°-7°.

EXAMPLE 9d

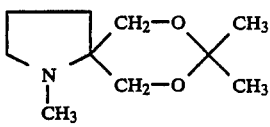
(xviii)

Compound (xvii) (20.5 g) produced as described in Example 9c was dissolved in 150 ml dry THF and added dropwise, at room temperature and under an atmosphere of $N_2$, to lithium aluminium hydride (3.9 g) in 50 ml dry THF. The reaction was then stirred at room temperature for 2 hours before cooling to 5° and adding ethyl acetate (to destroy excess $LiAlH_4$) followed by a saturated aqueous solution of potassium sodium tartrate. The resulting mixture was stirred vigorously for 20 minutes and then the organic layer separated. The aqueous solution was extracted with ethyl acetate and the organic layers combined, dried ($MgSO_4$) and evaporated "in vacuo" to yield a yellow oil which was distilled under high vacuum to give compound (xviii) as a colourless oil.

Yield 10.1 g (53%)
bp. 45°–50° at 0.4 mbar
NMR taken (1.4, 2s, 6H; 1.7, m, 4H; 2.5, s, 3H; 2.8, m, 2H; 3.5, d, 2H; 3.9, d, 2H)

Example 9e

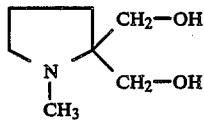
(xix)

Compound (xviii) (2.7 g) produced in Example 9d was dissolved in 20 ml 2N HCl (aq) and the resuling clear solution stirred for 2 hours at room temperature. Then 2.0 g sodium hydroxide was added and the product extracted with $CH_2Cl_2$ (in continuous extraction apparatus) for 3 hours. Evaporation "in vacuo" of the $CH_2Cl_2$ solution after this time gave compound (xix) as a waxy solid.

Yield 1.90 g (90%)
NMR taken (1.8, m, 4H; 2.4, s, 3H; 2.8, t, 2H; 3, 5, s, 4H; 3.8, s, 2H)

Example 9f

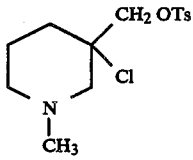
(xx)

TS = para-toluenesulphonyl 2.9 g para-toluenesulphonyl chloride was added portionwise, at room temperature, to compound (xix), (1.0 g) from Example 9e and triethylamine (1.5 g) in 10 ml $CH_2Cl_2$. The resulting solution was stirred at room temperature for 48 hours and then diluted with more $CH_2Cl_2$ and washed with water. The organic layer was separated, dried ($MgSO_4$) and evaporated "in vacuo" to yield an orange viscous oil. Purification by column chromatography on silica, using ethyl acetate as eluant, gave a yellow oil (1.2 g) which crystallised on standing. Recrystallisation from cyclohexane yielded compound (xx). mp. 91°–2°.

NMR: (1.8, m, 4H; 2.2, s, 3H; 2.5, m, 4H; 4.2, q, 2H; 7.4, d, 2H; 7.8, d, 2H)

Example 9g

Compound (xx) (6.0 g) produced as described in Example 9f, and sodium benzenethiosulphonate (7.4 g) were dissolved in ethanol (75 ml) and heated under reflux for 4 hours. The mixture was then filtered and the filtrate evaporated "in vacuo" to give a yellow sticky solid. This was chromatographed on silica using 1:1 60–80 petrol:ethyl acetate eluant, to give compound 9 as a yellow oil (3.6 g).

The yellow oil was dissolved in acetone and treated with an approximate 5.5M solution of hydrogen chloride in ethanol giving the hydrochloride salt of Compound 9 as a white solid. This was filtered, dried and recrystallised from acetone-ethanol to give pure hydrochloride salt (2.5 g). mp. 128°–30°.

EXAMPLE 10

This Example illustrates the preparation of compound 10 in Table (III).

Powdered sodium hydroxide (0.4 g) was dissolved in ethanol (20 ml) followed by compound (xxi) (below) (2.18 g) and potassium thiotosylate (4.52 g). The resulting mixture was heated under reflux for 4 hours, diluted with hot ethanol (20 ml) and filtered hot. The filtrate was cooled to room temperature giving crude product as a light yellow crystalline solid. This was filtered, washed with ethanol and recrystallised from ethanol to give compound 10.

Yield 1.40 g (29%)
mp. 107°–8°
NMR: 1.7, m, 4H; 2.2, s, 3H; 2.5, s, 6H; 2.7, m, 2H; 3.0, d, 2H; 3.15, d, 2H; 7.35, d, 4H; 7.8, d, 4H.

EXAMPLE 11

This Example further illustrates an alternative preparation of compound 9 in Table III.

Example 11a

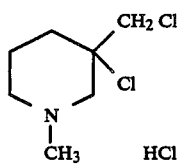
(xxi)

1-Methyl-3-piperidone was prepared by known literature methods (eg. JACS 55 1233–41 (1933)) and was used to prepare 1-methyl-3-methylene piperidine as described in Collection Czech. Chem. Comm. 32(1) 457–60 (1967) (CA 66 55351h).

1-Methyl-3-methylene piperidine (2.8 g) was dissolved in 50 ml dry diethyl ether and treated with dry hydrogen chloride to give the hydrochloride salt as a white precipitate. This was filtered, washed with dry $Et_2O$ and dried, "in vacuo", over $P_2O_5$ (the salt was very hygroscopic and exposure to the air was kept to a minimum). The resulting, dry, hydrochloride, 3.5 g, was dissolved in chloroform, 40 ml, and the solution cooled to 5° and treated, for approximately 1 hour, with chlorine gas. The green solution was allowed to warm to room temperature, stoppered and left overnight before evaporating "in vacuo" to give the crude product. Recrystallisation from acetone/ethanol yielded compound (xxi) in pure form.
Yield 2.7 g
mp. 181°–182°

Example 11b

Compound (xxi) (2.4 g) from Example 11a was dissolved in water (20 ml), and neutralised by the addition of 5.9 ml 2M sodium hydroxide. The solution was extracted with $CH_2Cl_2$ (4x) and the combined extracts dried ($MgSO_4$), and evaporated "in vacuo" at 25° to give the free base as a colourless oil. This was dissolved in ethanol (40 ml), sodium benzenethiosulphonate (4.6 g) added and the solution heated under reflux for 6 hours. Then filtered (hot) and the filtrate evaporated "in vacuo" to give a mixture of viscous oil and solid. Purification by medium pressure column chromatography on silica, using ethyl acetate: 60–80 petrol (1:1) eluant, produced a light yellow viscous oil which crystallised on standing. Recrystallisation from methanol yielded compound 9 as colourless plates.
Yield 1.1 g
mp. 77°–8°
NMR (1.7 m, 4H; 2.2, s, 3H; 2.7, t, 2H; 3.05, d, 2H; 3.15, d, 2H; 7.6, m, 6H; 7.9, m, 4H)

|      |            | C     | H    | N    |
|------|------------|-------|------|------|
| CHN: | % Expected | 49.86 | 5.06 | 3.06 |
|      | % Found    | 49.72 | 5.18 | 3.29 |

EXAMPLE 12

The following were prepared from 1-ethyl-3-piperidone hydrochloride by methods analogous to those described in Examples 11(a) and 11(b).
Compound No. 11 in Table III (mp. 76°–78° C.)
NMR: 1.0, t, 3H; 1.7, m, 4H; 2.4, q, 2H; 2.75, m, 2H; 3.05, d, 2H; 3.2, d, 2H; 7.6, m, 6H; 7.9, m, 4H
Compound No. 12 in Table III (mp. 108°–110° C.)
NMR: 1.0, t, 3H; 1.7, m, 4H; 2.4, q, 2H; 2.45, s, 6H; 2.7, m, 2H; 3.0, d, 2H; 3.2, d, 2H; 7.4, d, 4H; 7.8, d, 2H.

EXAMPLE 13

The following were prepared from N-benzyl-3-piperidone hydrochloride by methods analogous to those described in Example 11(a) and 11(b):
Compound No. 13 in Table III (mp. 133°–135° C.)
NMR: 1.7, m, 4H; 2.5, t, 2H; 3.1, d, 2H; 3.3, d, 2H; 3.5, s, 2H; 7.2, m, 5H; 7.6, m, 6H; 7.9, m, 4H
Compound No. 14 in Table III (mp. 107°–109° C.)
NMR: 1.6, m, 2H; 1.8, m, 2H; 2.45, s, 6H; 2.55, t, 2H; 3.1, d, 2H; 3, 3, d, 2H; 3.5, s, 2H; 7.2, m, 5H; 7.35, d, 4H; 7.8, d, 4H.

EXAMPLE 14

This Example illustrates the preparation of Compound 15 in Table IV.
The hydrochloride salt of Compound 9, (2.0 g) from Example 9 g was mixed with diethyl malonate (0.65 g) and triethylamine (1.3 g) in 10 ml chloroform and the mixture heated under reflux for 24 hours. The solution was then cooled to room temperature, diluted with more chloroform and washed with water (2x). The organic layer was separated, dried ($MgSO_4$) and evaporated "in vacuo" to give a red viscous oil. Purification by medium pressure column chromatography on silica, using diethyl ether eluant, gave compound 2 as a yellow crystalline solid. This solid was purified further by recrystallisation from 40–60 petrol.
Yield 270 mg (20%)
mp. 78°–80°
NMR: (1.3, m, 6H; 1.8, quin, 2H; 2.2, t, 3H; 2.3, d, 2H; 2.4, s, 3H; 2.9, t, 3H; 3.6, d, 2H; 4.3, m, 4H)

EXAMPLE 15

This Example illustrates the preparation of Compound 16 in Table IV.

Example 15a

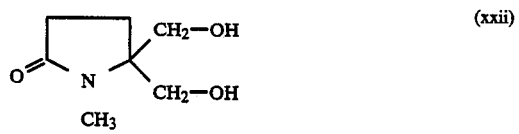

Compound (xvii) (107 g) prepared as described in Example 9c was dissolved in trifluoroacetic acid (158 g) and water (1000 ml) and stirred at room temperature for 2¼ hours. It was then left to stand overnight and evaporated in vacuo. The last traces of water were removed by azeotroping with toluene. The resulting viscous oil was dissolved in methanol (500 ml) and heated at 60°–70° for 2 hours. The methanol was then evaporated in vacuo to give an off-white solid. Recrystallisation from THF (300 ml) gave pure compound (xxii) as a white crystalline solid-76 g. mp. 94°–98°.

Example 15b

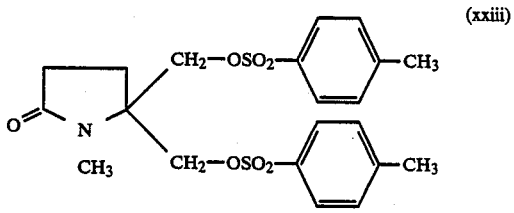

5.3 g para-toluenesulphonyl chloride was added portionwise, at room temperature to compound (xxii) (2.0 g) in 25 ml dry pyridine. The resulting red solution was stirred at room temperature for 5 hours and then left to stand overnight before adding a further 2.0 g para-toluenesulphonyl chloride and stirring for an additional 24 hours. The mixture was then poured into water to give a cream-coloured solid which was filtered, washed with water and dried-crude yield 5.5 g. Recrystallisation from 60–80 petrol and ethyl acetate gave pure compound (xxiii)-4.2 g. mp. 180°–1°.

Example 15c

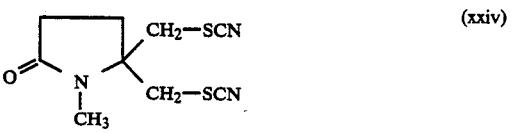

Compound (xxiii) (6.2 g) prepared as described in Example 15b and potassium thiocyanate (25 g) in 100 ml DMF were heated under reflux at 120°–130° for 20 hours. The solution was cooled to room temperature, poured into water to give a clear orange solution and extracted with CH$_2$Cl$_2$ (4x). The combined extracts were dried (MgSO$_4$) and evaporated in vacuo to give a light orange/brown solid. Trituration with ethanol, filtration and then recrystallisation from ethanol gave compound (xxiv) as pale brown needles-1.40 g. mp. 142°-3°.

NMR (2.1, m, 2H; 2.3, m, 2H; 2.6, s, 3H; 3.3, d, 2H; 3.6, d, 2H)

IR Strong-SCN at 2150 cm$^{-1}$

Example 15d

Compound (xxiv) (15.9 g) in 400 ml THF was added dropwise, under an atmosphere of N$_2$, to a suspension of LiAlH$_4$ (10 g) in 100 ml THF, cooled to 2° (slight exotherm). Reaction then allowed to warm to room temperature and left to stand overnight. EtOH then added, to destroy excess LIAlH$_4$, followed by saturated aqueous solution of sodium sulphate. The mixture was stirred vigorously for 15 minutes and then filtered and washed with CH$_2$Cl$_2$. The combined organic solutions were washed with water, dried (MgSO$_4$) and evaporated in vacuo to give a yellow oil-1.9 g. This was dissolved in ether, slurried with silica and filtered through a short pad of silica. Dry air was then blown through the solution for 4 hours at room temperature before evaporating in vacuo to give a yellow oil-1.4 g. The oil was purified by further column chromatography on silica using hexane-acetone (1:1) eluent to give Compound 16 as a yellow oil-570 mg NMR (1.8, m, 2H; 2.0, m, 2H; 2.4, s, 3H; 2.8, d, 2H; 3.2, d, 2H)

EXAMPLE 16

The following compounds were prepared from Compound 9 by methods analogous to those described in Example 14.

Compound No. 17 in Table IV (mp. 100°-1°)
NMR: 1.9, m, 2H; 2.2, m, 2H; 2.5, s, 3H; 2.5, d, 2H; 2.9, t, 2H; 3.6, d, 2H; 7.2, m, 2H; 7.8, dd, 2H.

Compound No. 18 in Table IV (mp. 66°-69° C.)
NMR: 1.4, t, 3H; 1.8, m, 2H; 2.2, m, 2H; 2.45, s, 3H; 2.55, d, 2H; 2.9, t, 2H; 3.5, d, 2H; 4.4, q, 2H

EXAMPLE 17

The following compound was prepared from Compound No. 10 in Table III by methods analogous to that described in Example 14:

Compound No. 18 in Table IV (mp. 57°-59° C.)
NMR: 1.1, t, 3H; 1.3, t, 6H; 1.8, m, 2H; 2.2, t, 2H; 2.3, d, 2H; 2.6, q, 2H; 2.9, t, 2H; 3.6, d, 2H; 4.3, m, 4H.

BIOLOGICAL DATA

The insecticidal activity of Compounds 1 to 19 is set out in the following Table V as a grading of 9, 5 or 0 where 9 indicates that 80–100% mortality was observed, 5 indicates that 50–79% mortality was observed and 0 indicates that 0–49% mortality was observed. The tests were conducted by spraying a suitable support medium (eg. leaves of a suitable food plant, or filter paper) and with a solution of the compound under test and placing the pests thereon. Assessment of mortality was made 72 hours after spraying. In the test the compounds were used in the form of aqueous composition prepared by dissolving the compound in mixture of solvents consisting of 4 parts by volume by acetone and 1 part by volume of diacetone alcohol and diluting the solution with water containing 0.01% by weight of a wetting agent ("Lissapol" NX-"Lissapol" is a Registered Trade Mark).

TABLE V

| Compound No. | Rate of Application | Species* CP | DB |
|---|---|---|---|
| 1 | 500 ppm | 9 | 9 |
| 2 | 500 ppm | 9 | 9 |
| 3 | 500 ppm | 0 | 9 |
| 4 | 500 ppm | 9 | 9 |
| 5 | 500 ppm | 9 | 9 |
| 6 | 500 ppm | 0 | 9 |
| 7 | 500 ppm | 9 | 9 |
|   | 100 ppm | 9 | 9 |
| 8 | 500 ppm | 5 | 9 |
| 9 | 500 ppm | 9 |   |
|   | 100 ppm | 0 | 9 |
|   | 500 ppm | 9 |   |
| 10 | 500 ppm | 9 | 9 |
| 11 | 500 ppm | 9 | 9 |
| 12 | 500 ppm | 9 | 9 |
| 15 | 250 ppm |   |   |
|   | 100 ppm | 9 | 9 |
| 16 | 500 ppm | 9 | 9 |
|   | 250 ppm | 0 | 9 |
| 17 | 500 ppm | 0 | 9 |
| 18 | 500 ppm | 9 | 9 |
| 19 | 500 ppm | 0 | 9 |

*CP = Chilo partellus
DB = Diabrotica balteata
All species were in the larval stage of growth In order to illustrate the nematocidal propeties of the compounds of Formula I, tomato plants (6–8 weeks old, variety 'Moneymaker') were planted out into soil infested with root-knot nematodes (Meloidogyne incognita) and the soil drenched with a composition of the compound under test (obtained by diluting 1 part of a solution of the compound in a 1:1 mixture of acetone and ethanol with 99 parts of water containing 1% of a wetting agent) at a rate of 200 ml/kg of soil. The roots of the plants were examined after 3 weeks to determine the reduction in the number of root knots as compared with a similar treatment omitting the compound. The results are given in Table VI as a grading of 0 to 9 where 0 represents from 0–10% reduction, 1 represents from 11 to 20% reduction, and so on up to 9 which represents 91 to 100% reduction in the number of root knots formed.

TABLE VI

| COMPOUND NO | RATE OF APPLICATION | GRADE |
|---|---|---|
| 2 | 12.5 ppm | 5 |
| 7 | 12.5 ppm | 7 |
| 9 | 12.5 ppm | 5 |
| 10 | 12.5 ppm | 4 |
| 15 | 12.5 ppm | 5 |
| 17 | 25 ppm | 0-1 |
| 18 | 12.5 ppm | 2 |

We claim:
1. A compound of formula (IB):

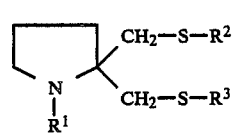

(IB)

or a salt thereof;
wherein
R$^1$ is alkyl, aralkyl or acyl; and $R^2$ and $R^3$ are $SO_2R^4$ is optionally substituted aryl, optionally substituted alkyl, aralkyl or cycloalkyl.

2. A compound according to claim 1 wherein $R^1$ is methyl, ethyl or benzyl.

3. An insecticidal or nematocidal composition comprising a compound of formula (IB) as defined in claim 1 in combination with an agriculturally acceptable carrier.

4. A method of killing or controlling insect or nematode pests which method comprises administering to the insect or to a locus thereof an effective amount of a compound of formula (IB) as defined in claim 1.

* * * * *